United States Patent [19]

Oftring et al.

[11] Patent Number: 5,739,301

[45] Date of Patent: Apr. 14, 1998

[54] 1-(2'-HYDROXY AND 2'-SULFATOALKYL) GLYCOSIDE

[75] Inventors: Alfred Oftring, Bad Dürkheim; Beate Strecker, Ludwigshafen; Günter Oetter, Frankenthal; Richard Schmidt; Wolfgang Klotz, both of Constance; Hendrik Wulff, Orsingen-Nenzingen, all of Germany

[73] Assignee: BASF Aktiengesellschaft, Ludwigshafen, Germany

[21] Appl. No.: 687,448

[22] PCT Filed: Feb. 4, 1995

[86] PCT No.: PCT/EP95/00402

§ 371 Date: Aug. 15, 1996

§ 102(e) Date: Aug. 15, 1996

[87] PCT Pub. No.: WO95/22551

PCT Pub. Date: Aug. 24, 1995

[30] Foreign Application Priority Data

Feb. 16, 1994 [DE] Germany .................. 44 04 728.2

[51] Int. Cl.$^6$ .................... C07H 15/04; C07H 1/00; A01N 43/04; A61K 31/70
[52] U.S. Cl. .................... 536/4.1; 536/118; 536/120; 536/124; 514/25
[58] Field of Search ................ 536/4.1, 118, 120, 536/124; 514/25

[56] References Cited

U.S. PATENT DOCUMENTS 4,287,078  9/1981  Langdon et al. .......... 536/120

*Primary Examiner*—John Kight
*Assistant Examiner*—Everett White
*Attorney, Agent, or Firm*—Oblon, Spivak, McClelland, Maier & Neustadt, P.C.

[57] ABSTRACT

1-(2'-hydroxy- and 2'-sulfatoalkyl)glycosides of formula I $$Gly-CH_2-\underset{\underset{X}{|}}{CH}-R \qquad (I)$$

where

X is a hydroxyl or a sulfato group of the formula $OSO_3M$, where

M is hydrogen, an alkali metal or an ammonium cation which can be substituted by organic radicals, R is a $C_6$- to $C_{30}$-alkyl or alkylene radical and Gly is the radical of a monosaccharide acetalized in the 1-position by the group designated above, are described.

The glycosides I are suitable as surfactants or emulsifiers in detergents, cleaning compositions or personal hygiene compositions.

10 Claims, No Drawings

1-(2'-HYDROXY AND 2'-SULFATOALKYL) GLYCOSIDE

The present invention relates to novel 1-alkylglycosides functionalized in the alkyl side chain, their preparation and their use as surfactants or emulsifiers in detergents, cleaning compositions or personal hygiene compositions.

Recently, mostly nonionic surface-active substances based on renewable raw materials have come to the fore to an increasing extent from the surfactant and emulsifiers sector. Substances of this type as a rule have good biodegradability, low toxicity and thus good environmental tolerability.

An important group of such nonionic surfactants are alkylglycosides, in which the long-chain hydrophobic alkyl radical is linked directly to the hydrophilic carbohydrate moiety of the molecule in the 1-position by means of an acetal bond. Indeed, such products already largely fulfill the expectations made of them, but in some properties such as foaming and wetting power, interfacial or surface tension or fat dissolving power still prove worthy of improvement.

A process for the preparation of O-(2-hydroxyalkylated) glucose derivatives by reaction of glucose provided with isopropylidene protective groups with alkyl-1,2-epoxides and subsequent removal of the protective groups is known from the reference Chem. Ber. 101, 3721–3723 (1968). This reference states that the position of the alkyl radical introduced into the glucose molecule in this way is unknown. The preparation of these O-alkylated glucose derivatives was of interest, in particular with respect to their interfacial activity and their biodegradability. Nothing is mentioned about possible real applications of these compounds.

It is an object of the present invention to provide nonionic surfactants or emulsifiers based on renewable raw materials, which no longer have the deficiences described above.

We have found that this object is achieved by 1-(2'hydroxy- and 2'-sulfatoalkyl)glycosides of the general formula I

where

X is a hydroxyl or a sulfato group of the formula $OSO_3M$, where

M is hydrogen, an alkali metal or an ammonium cation which can be substituted by organic radicals, R is a $C_6$- to $C_{30}$-alkyl or alkenyl radical and Gly is the radical of a monosaccharide acetalized in the 1-position by the group designated above.

The variable M, in addition to hydrogen, is an alkali metal or unsubstituted or substituted ammonium cation. Suitable sulfuric acid hemiester salts of this type are especially the lithium, potassium and, in particular, sodium salts, in addition also the unsubstituted ammonium salts and also organic amine salts having a tertiary nitrogen atom. Suitable bases on which organic amine salts of this type are based are, in particular, tertiary amines such as trialkylamines having 1 to 4 C atoms in the alkyl, eg. trimethyl- and triethylamine, and trialkanolamines having 2 or 3 C atoms in the alkanol radical, preferably triethanolamine, tri-n-propanolamine or triisopropanolamine.

The long-chain radical R is branched or preferably linear alkyl or alkenyl having, in particular, 8 to 20 C atoms, especially 9 to 16 C atoms. At a chain length of 10 to 14 C atoms for R, an optimum in the application properties is achieved, as obviously the optimum ratio is present here between hydrophobic and hydrophilic entities.

Examples of linear R radicals which may be mentioned are the following alkyl and alkenyl groups:

n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, eicosyl, hexadec-7-enyl, hexadeca-7,10-dienyl and hexadeca-7,10,13-trienyl.

Mixtures of various R radicals can also occur, for example mixtures of n-decyl and n-dodecyl or n-dodecyl and n-tetradecyl.

The monosaccharide radical Gly is built up from customary pentoses or hexoses. Carbohydrates Gly-H of this type are preferably aldopentoses such as ribose, arabinose, xylose and lyxose, aldohexoses such as allose, altrose, glucose, mannose, gulose, idose, galactose and talose, and ketohexoses such as fructose. Of these, mannose, glucose, galactose and fructose are preferred. Glucose is particularly preferred.

Normally the carbohydrates of the D-series occurring in nature are employed, however, representatives of the L-series can also be used.

The linkage of the carbohydrate components with the designated side chain takes place by means of an acetal bond to the anomeric C atom, ie. to the 1 C atom, it being possible for both α- and β-anomers to be present.

The glycosides I are advantageously prepared by reacting the monosaccharides Gly-H on which they are based with a cyclic sulfate of the general formula II

in the presence of a base and if desired hydrolyzing the 1-(2'-sulfatoalkyl)glycosides formed to the 1-(2'-hydroxyalkyl)glycosides.

The cyclic sulfates II are known and easily obtainable by simple syntheses starting from the corresponding olefin $CH_2=CH—R$.

Suitable bases are primarily strong bases such as, especially, hydrides, eg. sodium hydride, sodium borohydride or lithium aluminum hydride, but in addition also salt-like amides, eg. lithium diisopropylamide, alkoxides, eg. potassium tert-butoxide, sodium isopropoxide, sodium methoxide or sodium ethoxide, organolithiums, eg. alkyllithium compounds such as N-butyllithium or methyllithium, or alkali metal hydroxides, eg. sodium hydroxide, potassium hydroxide or lithium hydroxide. Mixtures of these bases can also be employed.

In a preferred embodiment, the reaction is carried out in a (compared with the cyclic sulfate II) inert, base-stable, polar organic solvent or a mixture of such solvents. Those suitable are particularly carboxamides such as 1,3-dimethyl-3,4,5,6-tetrahydro-2(1H)-pyrimidinone (DMPU), N,N-dimethylformamide (DMF), N,N-diethylformamide, N,N-dimethylacetamide, N,N-diethylacetamide or N-methylpyrrolidone (NMP). These solvents are expediently used in a form which is as anhydrous as possible.

The cyclic sulfate II as alkylating agent is customarily employed in equimolar or approximately equimolar ratio to the monosaccharide Gly-H or a small to moderate excess, for example up to 1.5 mol, in particular 1.35 mol, of II per mole of Gly-H is used. The base is also employed in equimolar or approximately equimolar amount or in an excess, for example up to 1.5 mol, in particular 1.25 mol, of base per mole of Gly-H.

As a rule, the reaction is carried out at normal pressure and at room temperature, ie. for example, at from 15° to 30°

C., but the reaction can also be carried out at slightly elevated temperature, for example at from 30° to 60° C., in order to accelerate the reaction. If the reaction is carried out at room temperature, it is normally complete after from 5 to 12 hours.

As a rule, working-up is carried out by decomposition of excess base, for example by addition of a proton-active compound, eg. of an alcohol, and isolation of the product I by distilling off the solvent and, if appropriate, chromatographic purification.

If it is wished to obtain the 1-(2'-hydroxyalkyl)glycoside I, the 1-(2'-sulfatoalkyl)glycoside I prepared by the process described is additionally hydrolyzed according to customary methods, for example by treating with catalytic amounts of a mineral acid such as sulfuric acid or equimolar amounts of an alkali metal hydroxide in a suitable medium such as an alcohol, water, dioxane, tetrahydrofuran or a mixture thereof, and, if desired, purified similarly as in the previous stage.

The 1-(2'-hydroxy- and 2'-sulfatoalkyl)glycosides I according to the invention are used as surface-active substances, ie. as nonionic or anionic surfactants, in detergents and cleaners, for example for cleaning processes in industry and the home such as for washing textiles or for cleaning processes in the foodstuffs sector such as the cleaning of beverage bottles or in washing-up liquids for use by hand. They are furthermore used as emulsifiers in personal hygiene compositions such as skin creams, lotions, gels, skin oils or hair shampoos.

The present invention also relates to detergents, cleaners and personal hygiene compositions which contain from 0.5 to 50% by weight, preferably from 1 to 30% by weight of such a glycoside I or a mixture of such glycosides I. The customary constituents and composition of detergents and cleaners and of personal hygiene compositions are known to the person skilled in the art and therefore do not need to be discussed further here.

The glycosides I according to the invention where $X=OSO_3M$ are anionic surfactants or emulsifiers which usually cause an effective lowering of the surface tension, have a very low critical micelle formation concentration and have a strong foaming power.

The glycosides I according to the invention where $X=OH$ are nonionic surfactants or emulsifiers which mostly have an unusually low interfacial tension, especially against ethereal oils (in applications in cosmetics as solubilizer), nonpolar oils such as motor oils (in applications in industrial cleaners) or fatty oils such as olive oil (when used in washing-up liquids for use by hand), which correlates very well with a high fat dissolving power, and cause an effective lowering of the surface tension and have a very low critical micelle formation concentration. They have a good wetting power for hard surfaces such as glass, metal, ceramic or plastic, which makes them suitable for appropriate cleaning compositions. What is additionally observed in them is a thickening action without the need for salt, which was hitherto unknown in the case of alkylglycosides, which makes them of particular interest for the cosmetic sector. They are furthermore distinctly more soluble in water than nonfunctionalized monoalkyl-glycosides of monosaccharides of identical alkyl chain length. As a rule, they have a very good wetting power, in particular on textile surfaces, and in the washing process usually produce very little foam, which makes them suitable for textile detergents, in particular powder detergents.

Since detergents, cleaning compositions and personal hygiene compositions generally contain mixtures of nonionic and anionic and, if appropriate, further surface-active substances, the two types of glycoside I according to the invention are useful components for establishing a certain property profile in these compositions.

The glycosides I according to the invention are based on pure monosaccharides and thus do not have the known problems which occur with alkypolyglycosides during preparation and use with respect to the purity, color or reproducibility of the composition.

The glycosides I according to the invention are biodegradable, nontoxic and thus have a good environmental tolerability.

EXAMPLES

General Working Procedure for Anomeric O-Alkylation with Cyclic Sulfates II 180 mg (1 mmol) of glucose and 1.8 mmol of alkylating agent II as in the table were dissolved in 10 ml of 1,3-dimethyl-3,4,5,6-tetrahydro-2(1H)-pyrimidinone (DMPU). After addition of 28.5 mg (1.2 mmol) of sodium hydride, the mixture was stirred at 20° C. for 8 h. The excess sodium hydride was then destroyed by means of a few drops of methanol. The reaction solution was again stirred for 1 h and then concentrated in a bulb tube oven (0.05 mbar, 100° C.). The residue was chromatographed on an $RP_{18}$ flash column.

General Working Procedure for Sulfate Elimination 1 mmol of the sulfuric acid hemiester sodium salt obtained in each case was suspended in 30 ml of dioxane and treated with 25 µl of sulfuric acid (0.1 mol/l). After stirring at 20° C. for 4 h, the reaction solution was neutralized with saturated sodium hydrogen-carbonate solution and concentrated under reduced pressure. The residue was chromatographed on a short $RP_{18}$ flash column.

The table shows the cyclic sulfates II employed, the yields of reaction products and, as characteristics of the products, the anomer ratio $\alpha:\beta$, the critical micelle formation concentration (CMC) and the surface tension $\sigma$.

TABLE

| Ex No. | Product | Yield [%] | α:β | CMC [mmol/l] | σ [mN/m] |
|---|---|---|---|---|---|
| | 1-(2'-Sulfatoalkyl)-glucoside | | | | |
| 1 | R = n-Decyl | 72 | 1:3 | 8.0 | 38.8 |
| 2 | R = n-Dodecyl | 72 | 1:3 | 2.7 | 37.3 |
| 3 | R = n-Tetradecyl | 65 | 1:3 | 0.6 | 43.0 |
| | 1-(2'-Hydroxyalkyl)-glucoside | | | | |
| 4 | R = n-Decyl | 82 | 1:3 | 0.17 | 28.2 |
| 5 | R = n-Dodecyl | 84 | 1:3 | 0.02 | 28.0 |
| 6 | R = n-Tetradecyl | 84 | 1:3 | —[1] | 27.8[2] |

[1] not measured
[2] measured at 40° C. (0.2 g/l); the other CMC values were determined at 25° C. (constancy)

The surface tension σ was determined as in DIN 53 914.

We claim:

1. A 1-(2'-hydroxy- or 2'-sulfatoalkyl)glycoside of the formula I

where

X is a hydroxyl or a sulfato group of the formula $OSO_3M$, where

M is hydrogen, an alkali metal or an ammonium cation which can be substituted by organic radicals, R is a $C_6$- to $C_{30}$-alkyl or alkenyl radical and Gly is the radical of a monosaccharide acetalized in the 1-position by the group designated above.

2. A 1-(2'-hydroxy- or 2'-sulfatoalkyl)glycoside I as claimed in claim 1, in which the variable Gly is the radical of an aldopentose, an aldohexose or a ketohexose.

3. A 1-(2'-hydroxy- or 2'-sulfatoalkyl)glycoside I as claimed in claim 1, in which the variable R is a $C_8$- to $C_{20}$-alkyl or -alkylene radical.

4. A process for preparing the 1-(2'-sulfatoalkyl)glycoside of formula I as claimed in claim 1, comprising reacting a monosaccharide of the formula Gly-H with a cyclic sulfate of formula II

 (II)

in the presence of a base.

5. The process as claimed in claim 4, wherein said base is a hydride.

6. A process as claimed in claim 4, wherein the reaction of the monosaccharide Gly-H with the cyclic sulfate of formula II is conducted in an inert, base-stable, polar organic solvent.

7. A process for preparing the 1-(2'-hydroxyalkyl) glycoside of formula I as claimed in claim 1, comprising reacting a monosaccharide of the formula Gly-H with a cyclic sulfate of formula II

 (II)

in the presence of a base; and hydrolyzing the sulfato group to a hydroxyl group.

8. The process as claimed in claim 7, wherein said base is a hydride.

9. A process as claimed in claim 7, wherein the reaction of the monosaccharide Gly-H with the cyclic sulfate of formula II is conducted in an inert, base-stable, polar organic solvent.

10. A detergent, cleaning composition or personal hygiene composition, comprising from 0.5 to 50% by weight of one or more 1-(2'-hydroxy- or 2'-sulfatoalkyl) glycosides I as claimed in claim 1 as surface-active substances or emulsifiers.

* * * * *